(12) United States Patent
Mandanis et al.

(10) Patent No.: US 10,017,234 B2
(45) Date of Patent: Jul. 10, 2018

(54) SYSTEM FOR DETERMINING A BENDING MOMENT ON AN OAR AND METHOD FOR DETERMINING THE POWER ON AN OAR

(71) Applicant: Mandanis angewandte Mechanik GmbH, Kriens (CH)

(72) Inventors: Georges Marie Mandanis, Kriens (CH); Cyrill Alexandre Mandanis, Stuttgart (DE)

(73) Assignee: MANDANIS ANGEWANDTE MECHANIK GMBH, Kriens (CH)

( * ) Notice: Subject to any disclaimer, the term of this patent is extended or adjusted under 35 U.S.C. 154(b) by 0 days.

(21) Appl. No.: 15/398,083

(22) Filed: Jan. 4, 2017

(65) Prior Publication Data
US 2017/0190404 A1  Jul. 6, 2017

(30) Foreign Application Priority Data

Jan. 4, 2016 (EP) ..................................... 16150045

(51) Int. Cl.
| | | |
|---|---|---|
| *B63H 16/04* | (2006.01) | |
| *B63H 16/10* | (2006.01) | |
| *A61B 5/22* | (2006.01) | |
| *A63B 24/00* | (2006.01) | |

(52) U.S. Cl.
CPC ............. B63H 16/04 (2013.01); A61B 5/224 (2013.01); A63B 24/0062 (2013.01)

(58) Field of Classification Search
CPC ................ B63H 16/04; B63H 2016/04; A63B 24/0062; A63B 24/0065; A63B 24/0068; A63B 24/0071; A61B 5/224

USPC .......................... 440/101, 102, 103; 434/247
See application file for complete search history.

(56) References Cited

U.S. PATENT DOCUMENTS

| | | | | |
|---|---|---|---|---|
| 4,984,986 A | * | 1/1991 | Vohnout ................. | A63B 24/00 434/247 |
| 5,099,689 A | * | 3/1992 | McGinn .................... | G01L 5/00 482/72 |
| 6,980,118 B2 | * | 12/2005 | Buvac .................... | A63B 69/08 340/689 |

(Continued)

FOREIGN PATENT DOCUMENTS

GB        2405947 A       3/2005

OTHER PUBLICATIONS

Search Report for European Application 16 150 045.9, dated Jul. 11, 2016.

*Primary Examiner* — Daniel V Venne
(74) *Attorney, Agent, or Firm* — Browdy and Neimark, PLLC (57) ABSTRACT

A system for determining a bending moment on an oar during a rowing stroke in the water has an oar handle, an oar shaft that extends from the oar handle, an oar blade that is disposed on the oar shaft on the side opposite the oar handle, at least one strain gauge, from the signal of which the bending moment can be determined, wherein the oar shaft is of a multi-part form and wherein a measuring sleeve, which joins the two adjacent parts of the oar shaft to each other and which comprises the at least one strain gauge, is disposed between two adjacent parts of the oar shaft. With a rotation measurement of the oar by an additional MEMS, the power against time of the rower can be determined by multiplication of the determined angular rate and the bending moment.

19 Claims, 7 Drawing Sheets

(56) References Cited

U.S. PATENT DOCUMENTS

| | | | |
|---|---|---|---|
| 7,114,398 B2 * | 10/2006 | Haines | A63B 24/00 440/106 |
| 8,192,242 B2 * | 6/2012 | Luecker | A61B 5/224 440/101 |
| 2010/0167606 A1 | 7/2010 | Luecker et al. | |
| 2011/0223816 A1 | 9/2011 | Boukas | |

* cited by examiner

SYSTEM FOR DETERMINING A BENDING MOMENT ON AN OAR AND METHOD FOR DETERMINING THE POWER ON AN OAR

TECHNICAL FIELD

The present invention concerns a system for determining a bending moment, a rowing power and a method for determining a rowing power of a rower on an oar during a rowing stroke in the water.

PRIOR ART

From US 2010/0167606 A1, an oar is known with which the force that is acting on an oar blade while rowing is determined by means of a deflection sensor and a temperature sensor and a processor. The sensors are integrated within the interior of the oar, which requires expensive assembly.

From US 2011/223816 A1, a multi-part oar is known with which a driven vane wheel that produces thrust is provided between the oar blade and the oar shaft.

From GB 2,405,947 A, a force measurement cell is known that is provided between a vertical pin of a supporting foot that is disposed on a rowing boat and a rowlock that is disposed by means of sleeves on the vertical pin, in order to be able to detect the forces acting on the oar with strain gauges.

DESCRIPTION OF THE INVENTION

It is therefore inter alia an object of the invention to provide an oar with which the assembly of the sensor is simplified, and that is more reliable, more advantageous or simpler to operate.

This object is achieved by a system with the features of claim 1. Said system enables for example the monitoring of the rowing strokes when the rower is training or competing by the rower himself or by a third person, such as for example a trainer. It enables a detailed analysis of the stroke with the aim of improving the stroke. It also enables a comparison with stored values, such as with those of an earlier series of measurements, for example of earlier training or racing, or enables a comparison with other rowers, for example with a team colleague or a world champion. Said comparisons help the rower or the trainer to be able to better estimate the power of the individual rower and thereby to put together specific training. The system is also suitable for leisure rowers, because it makes their own power and thereby their development identifiable.

In a preferred embodiment, for determining a bending moment on an oar during a rowing stroke in the water, the system comprises an oar handle, an oar shaft that extends from the oar handle, an oar blade that is disposed on the oar shaft on the side opposite to the oar handle, and at least one strain gauge (also referred to here in brief as a DMS), from the signal of which the bending moment can be determined, wherein the oar shaft is of a multi-part form and wherein a measuring sleeve is disposed between two adjacent parts of the oar shaft, which connects the two adjacent parts of the oar shaft to each other and which comprises the at least one strain gauge. Alternatively, the force on the oar blade can be determined with the same system. The stroke rate of the rower, i.e. the number of rowing strokes against time, can also be determined with the system.

Said design has inter alia the advantage that the measuring sensors can be simply integrated within the oar and it significantly simplifies the assembly as a result.

The central part forming the measuring transducer is sometimes referred to as a sleeve; it can also be referred to as a measuring bush. The bush is between the part on the oar handle side and the part on the oar blade side and contains sensors and all the systems that are necessary for sending the measurement signals (bending moment against time and rotation rate against time) to an analysis unit. The invention is based inter alia on the fact that for determining the rowing power the oar is divided into two pieces, namely into the part on the oar blade side and the part on the oar handle side, and a measuring bush is installed between these in order to determine two measurement values, namely the bending moment and the rotation rate; both measured against time in order to determine the desired variables of the rowing power. During this, it is essential for determination of the value to work over time intervals of a stroke, and the force alone or the torque is not of interest. For this purpose, the torque and rotation rate are measured in parallel against time at the same location, namely in the measuring bush.

Preferably, the measuring sleeve is essentially of a cylindrical form with a central axis and comprises a central part and two connecting parts for connecting to the two adjacent parts of the oar shaft, wherein the connecting parts are disposed on opposite sides of the central part. Because in general the oar shaft has an essentially circular cross section, a cylindrical shape is suitable as a connecting element. Alternatively, measuring sleeves with oval or rectangular cross section, such as for example rectangular, square or hexagonal cross section, can be used.

The measuring sleeve preferably comprises at least one recess, for example in the form of a flat section, on the periphery in the central part for accommodating the at least one strain gauge. The recesses enable the attachment of the strain gauges to a planar area and at the same time protect the strain gauges against mechanical influences, because in cross section the strain gauges lie within the outer circumferential lines of the measuring sleeve.

It is advantageous if the measuring sleeve comprises in the central part in the direction of the central axis two mutually opposite recesses on the outer periphery for accommodating a strain gauge each. Three, four, five, six or more uniformly or non-uniformly distributed recesses can be provided on the periphery, of which each can accommodate a respective strain gauge. Advantageously, the two mutually opposite recesses are designed and oriented so that they comprise a supporting surface for the strain gauge, which lies in a plane that is essentially parallel to a plane in which the oar blade extends. The largest strains can be measured in said supporting surface because of the direction in which force is introduced into the oar blade, i.e. essentially perpendicular to the oar blade.

Alternatively, the strain gauges can be disposed not in recesses but directly on the outer periphery of the measuring sleeve. A further alternative provides the arrangement of the strain gauges in the interior of the measuring sleeve if the sleeve comprises recesses provided for this in the interior thereof. Such inner recesses can extend along the longitudinal axis of the measuring sleeve and can for example be bores that extend from one side to the interior of the measuring sleeve. Said bores can extend over a region of the length of the measuring sleeve or over the entire length thereof.

In the case of two opposing strain gauges on the periphery of the measuring sleeve, said strain gauges measure the local strains, and the difference of said strains is proportional to the bending moment that is produced by a force acting on the oar blade.

Preferably, the two connecting parts are offset relative to the central part and the central part forms a stop for the two adjacent parts of the oar shaft. This enables the connecting parts to be easily inserted into the adjacent parts of the oar shaft and to be joined to said parts. For a secure connection, a thread can be provided. The stop prevents the connecting parts from being inserted into the shafts of the oar unsatisfactorily. Moreover, the stop increases the area of the connecting point and thereby improves the joint between the measuring sleeve and the oar shaft.

The measuring sleeve can comprise a central bore that extends along the central axis through the entire measuring sleeve. Alternatively, it can extend only over a certain length along the central axis, so that the measuring sleeve is closed on the one side. The central bore enables an internal feed of cables of the strain gauge to further electronic components, enables the feed of cables from further electronic components or enables the accommodation of further electronic components. The central bore can also be used to accommodate the strain gauges. However, in that case the sensitivity reduces greatly if the bore does not have such a large internal diameter that the measuring sleeve is only left with a thin cover.

In another preferred embodiment, the measuring transducer comprises a radial slot that is oriented in the longitudinal direction of the measuring transducer, in which a circuit that is connected to the strain gauge(s) is inserted. In this case, the slot can optionally not be a blind hole, but can comprise at least one through opening for connecting the inserted circuit to one or more strain gauges that are disposed near the opening through the measuring transducer itself. Advantageously, in that case the space is made further use of as a result of an energy source being inserted into the slot in addition to the circuit. In that case the circuit or processing unit can also comprise a microelectromechanical system or acceleration sensor that is designed to measure the rotational motion of the oar and to transmit a corresponding signal wirelessly to at least one receiver, either together with the torque value or even on its own.

In a preferable embodiment, the oar shaft is in two parts and is divided into a part on the oar blade side and a part on the oar handle side, wherein the part on the oar blade side comprises, on the end thereof opposite the oar blade, a collar with a ring for attaching the oar to a rowing boat and wherein the measuring sleeve is then joined to the collar with the part on the oar blade side. The rowlock is the accommodating element for the oar on the boat. Said arrangement enables simple assembly, and cables and any electronic components can be easily accommodated in the part on the oar handle side. The subsequent arrangement of the measuring sleeve on the collar with the ring is to be preferred, because in said region the elongation of the oar shaft or the measuring sleeve is greatest and thereby the strain gauge has a greater signal range, which results in greater accuracy of the measurement results.

Alternatively, the oar shaft is in two parts and is divided into a part on the oar blade side and a part on the oar handle side, wherein the part on the oar handle side comprises a collar with a ring for attaching the oar to a rowing boat on the end thereof opposite the oar handle, and wherein the measuring sleeve is subsequently joined to the collar with the part on the oar handle side.

Alternatively, the oar shaft can comprise three, four or more parts and one or more measuring sleeves can be disposed between two respective adjacent parts of the oar shaft in order to join the respective two adjacent parts of the oar shaft to each other. By the arrangement of a plurality of measuring sleeves along the oar shaft, the elongation of the oar shaft over the length, or of the measuring sleeves at the respective locations, can be determined.

Preferably, the measuring sleeve is glued into the two adjacent parts of the oar shaft. Said permanent joint is space-saving, light and is characterized by high strength. Alternatively, the measuring sleeve can be reversibly joined to the adjacent parts, for example by a threaded, rotational or plug connection. Because of such a reversible joint, the oar can be broken down into several parts, as a result of which less space is required for storage, for example.

The measuring sleeve preferably comprises two mutually opposite strain gauges on the periphery for measuring the elongation at the surface of the measuring sleeve. Using said arrangement, the elongation of the oar shaft or of the measuring sleeve can be measured on the one side and the compression can be measured on the opposite side.

Alternatively, three, four or more strain gauges can be used, which can be disposed in the recesses provided for this on the periphery. With the arrangement of a plurality of strain gauges on the periphery, the direction of the force action on the oar can be determined. With four strain gauges at a regular angular separation of 90 degrees, only two opposing strain gauges that are essentially disposed perpendicular to the direction of motion (i.e. following the pivoting of the oar) are under traction and compression during a stroke, whereas the other two strain gauges, apart from an inclination of the oar, are disposed essentially horizontal to the water surface/bottom of the boat and do not experience any larger forces and torques in the measurement direction thereof.

In a preferred embodiment, the system further comprises a processing unit that is electrically conductively connected by cable to the at least one strain gauge, and comprises at least one energy source that is electrically conductively connected to the at least one strain gauge and the processing unit in order to supply the at least one strain gauge and the processing unit with electrical energy. The processing unit comprises a DMS amplifier that is designed to amplify a signal produced by the at least one strain gauge and to wirelessly transmit said signal to at least one receiver, especially by a wireless transmission by means of Bluetooth to a locally disposed unit. The analysis could also be carried out on the oar itself and displaying the results on the oar itself is also possible. In that case, the display and input unit are provided on the oar, for example a holder for a smartphone could also be provided on the oar; this can be considered to be an additional option. In this respect, wireless transmissions, for example via Bluetooth or cable connections, to locally disposed units are in particular possible configurations.

Preferably, the processing unit comprises a microelectromechanical system (MEMS) that is designed to measure the rotational motion of the oar during a rowing stroke in the water and to transmit a corresponding signal to at least one receiver, for example wirelessly. However, a wire connection is also possible, for example to a smartphone that can be attached to the oar. In addition to the torque measurement, the necessary rotation measurement is also carried out in a simple manner for determining the rowing power.

With the wireless transmission of the signals to an external receiver, i.e. to a device that is not fixedly joined to or integrated within the oar, a robust system that is insensitive to mechanical influences can be provided. In addition, such a system enables the flexible use of the signals that are provided by one or more receivers.

The processing unit is preferably disposed in the part of the oar shaft on the oar handle side. Alternatively, the processing unit can be disposed in the part on the oar blade side of the oar shaft.

The at least one receiver is preferably a desktop, a laptop, a tablet or a smartphone or the at least one receiver is a unit, for example a USB stick, that can be connected to a desktop, a laptop, a tablet or a smartphone.

In the case of the integration of the receiver into the oar as well as in the case of a receiver essentially independent of the oar, the transmitted signals can not only be received and analysed, they can also be stored for later use. The development of a rower can thereby be displayed and analysed.

The corresponding receiver comprises a program or an app that can be used with the transmitted signals, for example to determine the stroke rate and/or the rowing power, to enable monitoring of the determined data and other comparison operations.

A cover or protective sleeve for protecting the measuring sleeve or the strain gauge that is disposed on the measuring sleeve can be disposed on or around the measuring sleeve or the strain gauge.

The microelectromechanical system MEMS, the DMS measurement amplifier and transmitter and the energy source can be provided separately from the sleeve. In other series, for practical and technical reasons the three aforementioned elements are integrated within the cylinder of the measuring transducer.

A preferred method for determining the power on an oar during a stroke by a rower in the water comprises the following steps:
  determining the bending moment on the oar against time by means of at least one strain gauge that is disposed on a measuring sleeve that is disposed between two adjacent parts of an oar shaft of the oar and that joins the parts to each other;
  determining the rotational movement of the oar about an axis parallel to the bending moment vector against time by means of a microelectromechanical system that is disposed on the oar; and
  determining the rowing power against time from the product of the bending moment and the rotational movement.

Determining the rotational movement of the oar about an axis parallel to the bending moment vector against time can require in relation to the time detection that the time is measured, during which the strain gauges for determining the bending torque are essentially parallel to the rowlock axis during said measurement, whereas they are essentially perpendicular to the rowlock axis during the return oar movement without a force action. In that case, the microelectromechanical system detects said pulling time and the angle covered, and the rotation rate is multiplied by the bending moment for determining the power, wherein it is a scalar product of the magnitudes of the two vector values. Here the rowlock axis, i.e. the axis about which the rowlock rotates, is considered to be the main axis of the oar.

Preferably, two mutually opposite strain gauges are provided on the periphery of the measuring sleeve in order to determine the local strains.

The following equation applies to the calculation of the rowing power against time:

$$L(t)=M(t)\cdot\omega(t)$$

if the vector M(t) is parallel to ω(t). In other words: here L(t) is the scalar product of the vectors M(t) and ω(t).

In this case, M(t) is the bending moment on the oar in Newton-meters against time. Thus L(t) is the scalar product of M(t)//ω(t) and the following applies:

$$M(t)=A\cdot[DMS\_1(t)-DMS\_2(t)]$$

wherein A is a proportionality factor and wherein DMS_1(t) is a measurement signal of a first strain gauge against time and wherein DMS_2(t) is a measurement signal of a second strain gauge against time,
wherein ω(t) is the angular rate of the rotational movement of the oar against time and the following applies:

$$\omega(t)=d\varphi(t)/dt$$

wherein φ(t) is the angle of rotation of the rotational movement of the oar in radians about an axis parallel to the torque vector against time.

An advantage of the apparatus is that temperature effects do not have to be compensated. When starting the measurement, the measurement value for a "zero" oar force is set to "Null". During the measurement, the temperature of the measuring sleeve has stabilized, so that no temperature disturbance is to be feared. Optionally, additional unloaded DMSs can be installed in the measuring sleeve, for example transverse to the aforementioned DMSs, so that the temperature effect is fully compensated.

Further embodiments are specified in the dependent claims.

BRIEF DESCRIPTION OF THE DRAWINGS

Preferred embodiments of the invention are described below using the drawings, which are only used for explanation and are not to be construed as limiting. In the drawings.

DESCRIPTION OF PREFERRED EMBODIMENTS

Figure 1:
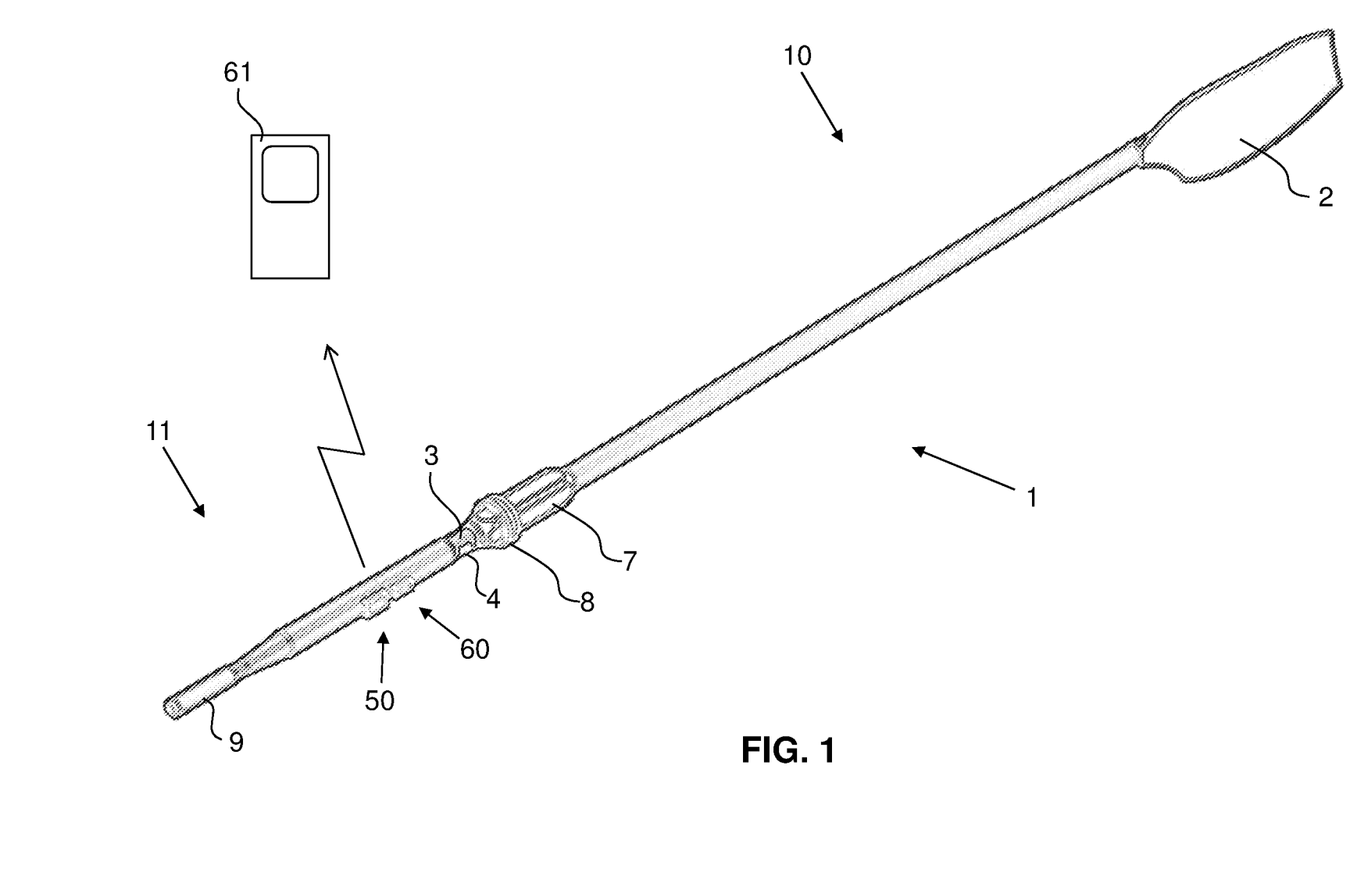
FIG. 1 shows a perspective view of a system according to an exemplary embodiment of the invention with an oar and a receiver.

FIG. 1 shows a perspective view of a system according to the invention with an oar and a receiver 61. The oar comprises an oar handle 9 and an oar shaft 1 that extends from the oar handle 9. The oar further comprises an oar blade 2 that is disposed on the oar shaft 1 on the side opposite the oar handle 9. The oar shaft 1 is of a multi-part form, wherein a measuring sleeve 3 is disposed between two adjacent parts of the oar shaft 1 that joins the two adjacent parts of the oar shaft 1 to each other and that comprises the at least one strain gauge 4. The oar shaft 1 represented in FIG. 1 is in two parts and is divided into a part on the oar blade side 10 and a part 11 on the oar handle side. The part on the oar blade side 10 comprises a collar 7 on the end thereof opposite the oar blade 2 with a ring 8 for attaching the oar to a rowing boat. The measuring sleeve 3 is then joined to the collar 7 with the part of the oar shaft 1 on the oar blade side 10. A processing unit 50 and an energy source 60 on the outside thereof are illustrated on the part 11 of the oar shaft 1 on the oar handle side. These can, however, also be disposed in the interior of the oar shaft 1, and in this case are not externally visible.

Figure 2:
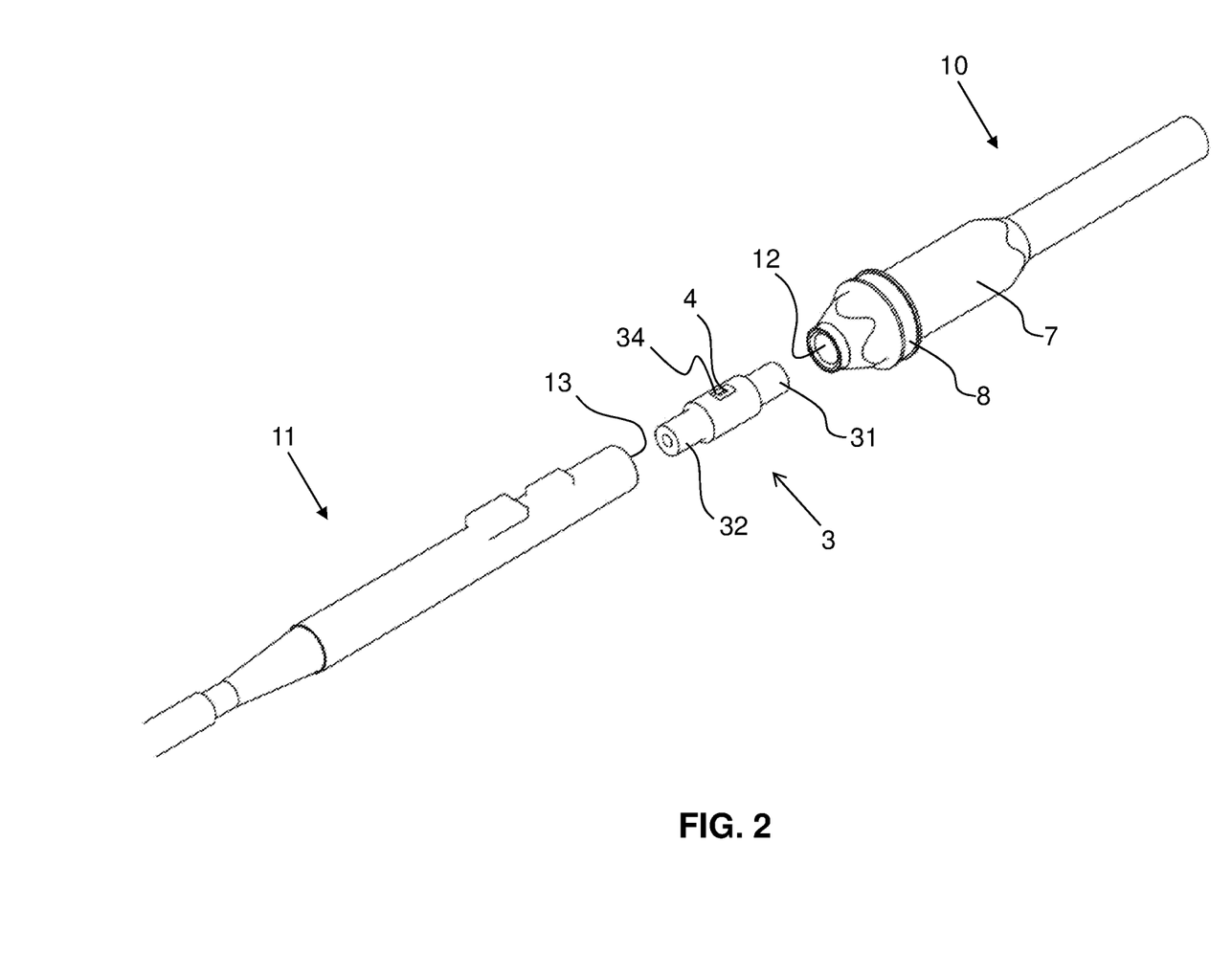
FIG. 2 shows a perspective exploded view of parts of an oar shaft of the oar and of a measuring sleeve of FIG. 1.

FIG. 2 shows a perspective exploded view of the parts of the oar shaft 1 and of the measuring sleeve of FIG. 1, wherein relative to FIG. 1 the represented parts and the measuring sleeve are rotated by 90 degrees relative to the longitudinal axis of the oar shaft 1. The measuring sleeve 3 is essentially of a cylindrical form and comprises a central part 30 and two connecting parts 31, 32 for joining to the two adjacent parts of the oar shaft 1, wherein the connecting parts 31, 32 are disposed on mutually opposite sides of the central part 30 in relation to the longitudinal direction of the measuring sleeve 1.

The measuring sleeve 3 comprises at least one recess 34 in the central part 30 on the periphery for accommodating the at least one strain gauge 4. The recess 34 is a flat section of the periphery of the central part 30, wherein there is a planar area that is used for the arrangement of a strain gauge 4. On the opposite side of the central part 30 in relation to the periphery, a recess is provided that is not represented and that is identical to the recess 34, as shown in FIG. 3.

The part of the oar shaft 1 on the oar blade side 10 comprises a recess 12 on the oar blade side on the side thereof opposite the oar blade 2 for accommodating a first connecting part 13 of the two connecting parts. The part of the oar shaft 1 on the oar handle side 11 comprises on the side thereof opposite the oar handle 9 a recess 13 on the oar handle side that is not represented for accommodating a second connecting part 32 of the two connecting parts.

Figure 3:
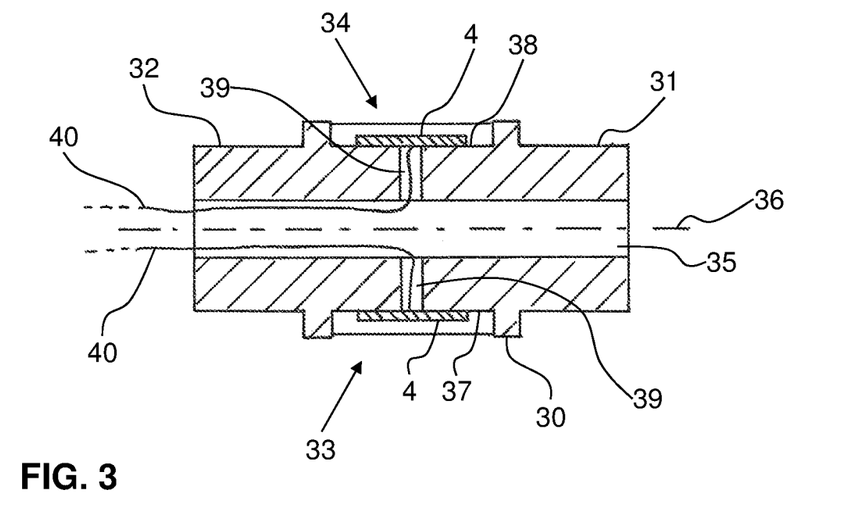
FIG. 3 shows a sectional view of the measuring sleeve of FIG. 2 with two strain gauges.

FIG. 3 shows a sectional view of the measuring sleeve 3 of FIG. 2 with two strain gauges 4. The essentially cylindrical measuring sleeve 3 comprises a main body that is rotationally symmetrical in relation to the central axis 36. The connecting parts 31, 32 are offset in relation to the central part 30, i.e. the connecting parts 31, 32 have a smaller external diameter in cross section than the central part. The central part 30 thereby forms a lateral stop in relation to the central axis 36 on each of the two ends thereof, with which each of the two adjacent parts of the oar shaft 1 can come into contact. The measuring sleeve 3 comprises two mutually opposite recesses 33, 34 on the outer periphery in the central part 30 in the direction of the central axis 36 for accommodating a strain gauge 4 each. As a result of the design of the recesses, there are planar supporting surfaces on the surface of the measuring sleeve that are mutually opposite on the periphery. A first recess 33 comprises a first supporting surface 37 and a second recess 34 comprises a second supporting surface 38 that is essentially parallel to the first supporting surface 37. The strain gauges 4 are disposed on the supporting surfaces 37, 38. The measuring sleeve 3 comprises a central bore 35 that extends along the central axis 36 through the entire measuring sleeve 3. Radial bores 39 lead from the supporting surfaces 37, 38 to the central bore 35. The radial bores 39 together with the central bore 35 form a channel for guiding cables 40 of the respective strain gauges 4 in the interior of the shaft.

Figure 4:
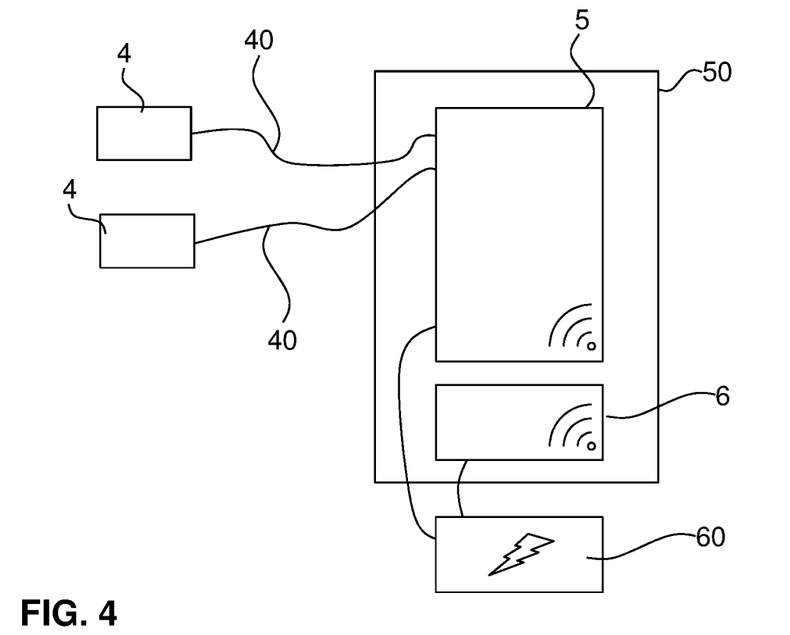
FIG. 4 shows a schematic representation of a processing unit according to the invention and the energy source connected thereto and the strain gauge connected thereto.

FIG. 4 shows a schematic representation of a processing unit 50 according to the invention and the energy source 60 connected thereto and the strain gauges 4 connected thereto. The processing unit 50 comprises a DMS amplifier 5 that is designed to amplify a signal produced by a strain gauge 4 and to transmit said signal wirelessly to at least one receiver 61. The processing unit 50 further comprises a microelectromechanical system 6 (MEMS) that is designed to measure the rotational motion of the oar and to transmit a corresponding signal wirelessly to a receiver 61, as shown in FIG. 1. It is essential to use the acceleration sensors to detect the essentially horizontal movement of the oar (apart from immersion and lifting out). The rotary motion of the oar about the longitudinal axis of the oar can be but does not have to be included in the measurement.

The connections between the strain gauge 4 and the DMS amplifier 5 or between the energy source 60 and the DMS amplifier 5 or between the energy source 60 and the MEMS 6 are in the form of cables 40. For the torque measurement, the strain gauges 4 are connected to the amplifier 5, which is connected to the transmitter. An energy source supplies the amplifier and the transmitter. The apparatus for the rotation measurement is completely separate according to the represented implementation. The microelectromechanical system 6 (about the same size as a USB stick) is provided in the small rectangle and the gyroscope and the transmitter are installed therein.

One DMS amplifier 5 is sufficient for the two strain gauges 4. A DMS amplifier 5 can be provided for each strain gauge 4. The DMSs 4 can also be connected in a circuit of the Wheatstone bridge type, so that it cannot be said that each DMS needs an amplifier. The current of the circuit is amplified.

With the MEMS 6, as with the amplifier 5, the symbol for wireless transmission concerns the transmission to an external analysis unit, which for example can be a smartphone etc. In principle, analysis in a printed circuit on the oar would also be possible, in which case only results would be transmitted for (visual/audible) display.

Figure 5:
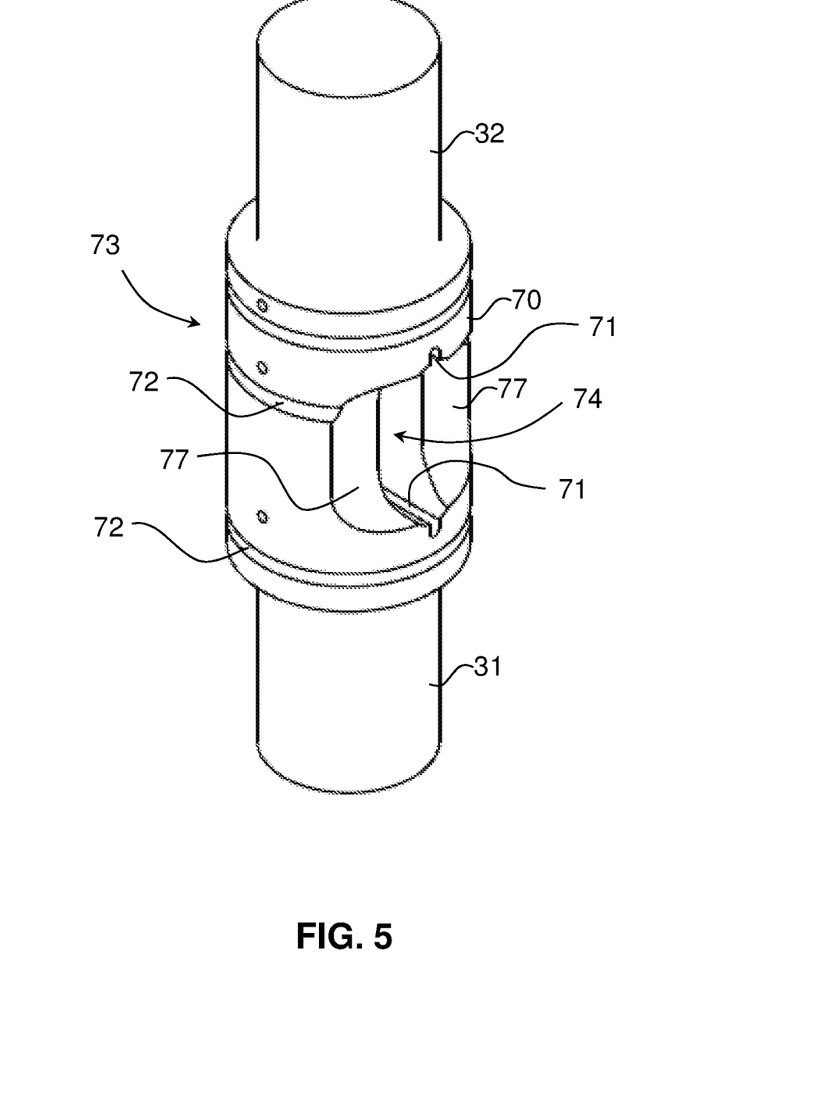
FIG. 5 shows a perspective view of a measuring sleeve for a system according to a further exemplary embodiment of the invention.
Figure 6:
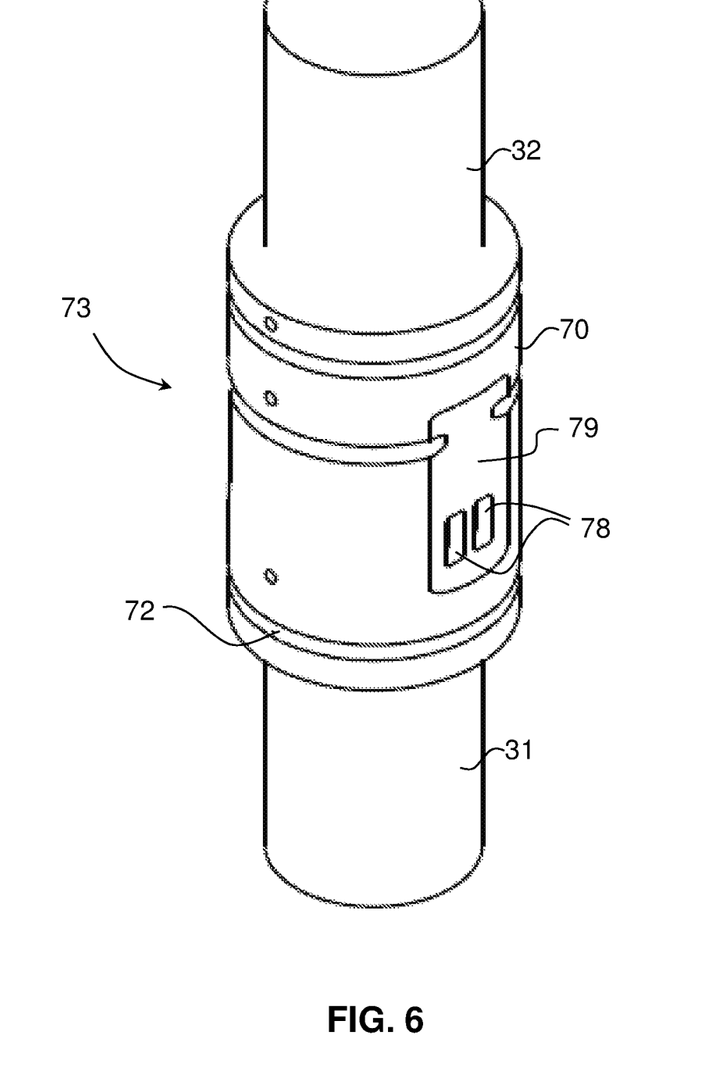
FIG. 6 shows a perspective view of the measuring sleeve according to FIG. 5, which is rotated by 180 degrees along the longitudinal axis thereof.

FIG. 5 shows a perspective view of a measuring transducer 73 for a system according to a further exemplary embodiment the invention, similar to the measuring sleeve 3 of FIG. 2. Identical and similar features are given the same description with the same or similar reference characters. FIG. 6 shows a further perspective view of the measuring transducer 73 according to FIG. 5, which is rotated by 180 degrees along the longitudinal axis thereof in this case.

The measuring transducer 73 comprises a central part and two connecting parts 31 and 32. Said connecting parts are, as with the measuring transducer according to FIG. 2, connected in the case of the first connecting part 31 to the part on the oar blade side 10 of the oar shaft 1 and in the case of the second connecting part to the part 11 on the oar handle side. For this purpose, as in FIG. 2, a recess 12 on the oar blade side for accommodating the first connecting part 31 and a recess 13 on the oar handle side for accommodating a second connecting part 32 are provided. The connection can be a threaded joint, an adhesive joint or a snap-fitting positive-locking joint. Advantageously, it is reversible.

Advantageously, radial grooves (or even ribs) 72 are provided in order to reversibly provide the central part with a clip-on cover in order to protect the electronics in the recess 74 or the perforations 78, which are described below.

The measuring transducer 73 comprises at least one radial recess 74 on the periphery in the central part 70 for accommodating the at least one strain gauge 4. The radial recess 74 is a hole with an oval cross section that also comprises at the opening thereof a flat section 77 of the central part 70 that enables a higher protruding free end of a component pushed into the recess, which greatly improves the operation of an antenna provided there, which is part of a printed circuit in the form of a plug-in board that is not represented in the figure. The printed circuit is a rectangle and has two opposing lateral edges. Said lateral edges are at a predetermined distance from each other that corresponds to the distance of two opposing grooves 71 in the shorter end surface of the recess 74, which has an oval or rectangular cross section, so that the printed circuit can be inserted into a frictional joint between the grooves 71. Two strain gauges are attached to the left and right on the flat section 77 next to the recess 74.

Two further strain gauges are attached to the flattened area 79 adjacent to each other, in particular next to each other and above the openings 78, into which the connecting cables can be inserted in that case. In principle, this would also be possible via a single opening or around the middle part 70.

The radial recess 74 is substantially a blind hole, "substantially" because at least one through hole 78 is provided far down and over the centre of the element; in this case there are two oval or rectangular through holes 78, in particular at two opposing positions to the radial extension of the recess 74, so that two plugs that are provided on the printed circuit on both sides protrude into said through holes 78, which are disposed parallel to each other.

For a measuring transducer 73 represented here in the drawings, the three aforementioned elements, i.e. the MS measurement amplifier, the transmitter and an energy source 60, have been integrated within the sleeve for practical and technical reasons. The processing unit 50 described further above further comprises a microelectromechanical system 6 that is designed to measure the rotational motion of the oar and to transmit a corresponding signal wirelessly to a receiver 61, as shown in FIG. 1.

FIGS. 5 and 6 show the four significant features of the exemplary embodiments described here. The mechanical part consists of the elements of the measuring beam, on which four DMSs are glued and in a central cut-out of which the aforementioned elements 5, 6 and 60 are accommodated, an adapter 31 with a thread for connecting to the part on the oar handle side and a further adapter 32 with a thread for connecting to the part on the oar blade side.

The print circuit board (PCB), on which the aforementioned elements 5 and 6 are provided, and the energy source 60 are not shown in the image of FIG. 5. The energy source 60 can in particular be pushed into the cut-out 74 as a flat accumulator next to the PCB. In that case a cable connection is provided between the accumulator and the PCB.

The measuring transducer no longer has a central axial bore, in contrast to the exemplary embodiment according to FIGS. 2 and 3. The flattened areas for accommodating the DMSs are not identical in relation to the central plane that is perpendicular to the plane of symmetry. The upper flat section has been cut out deeper in order to allow free space for a transmitter antenna on the PCB that protrudes into said space, in addition to better manageability.

Figure 7:
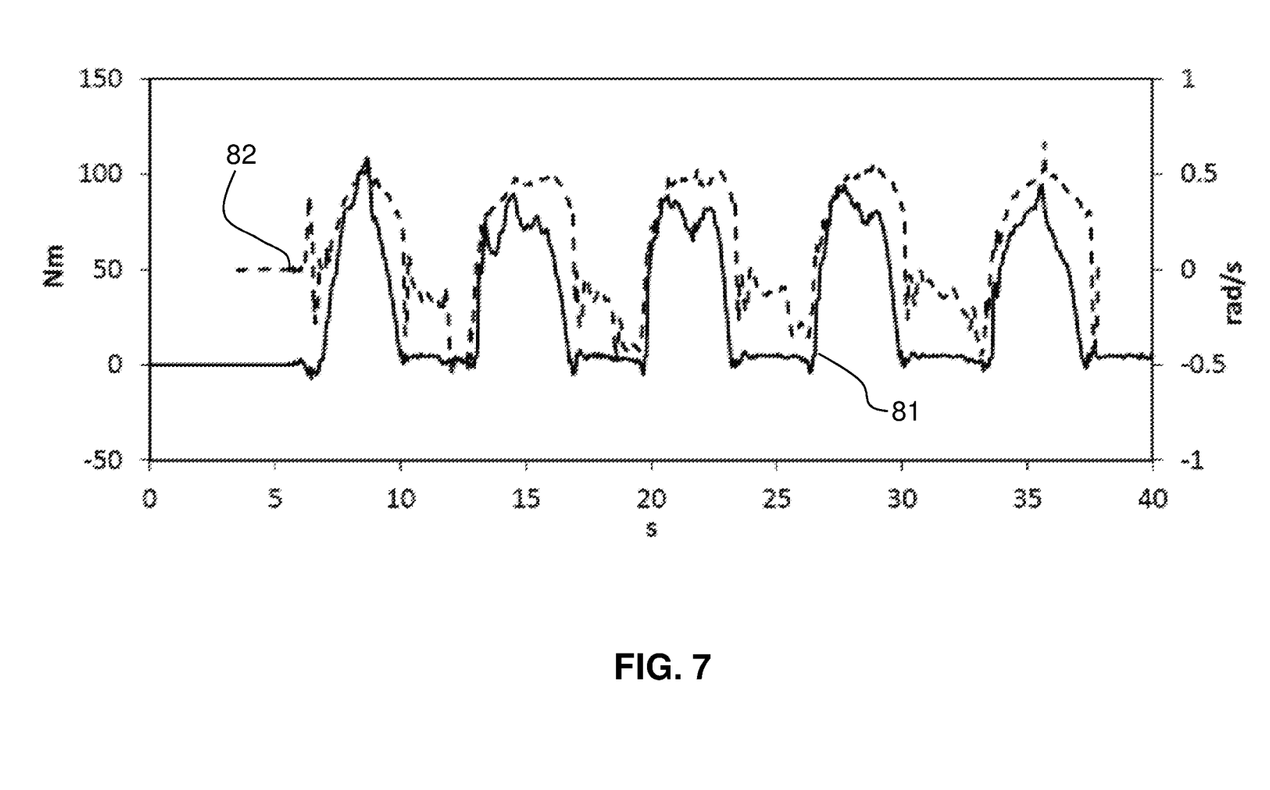
FIG. 7 shows measurement graphs of torque and rotation rate of an oar during the practical operation of a measuring transducer according to FIG. 5.
Figure 8:
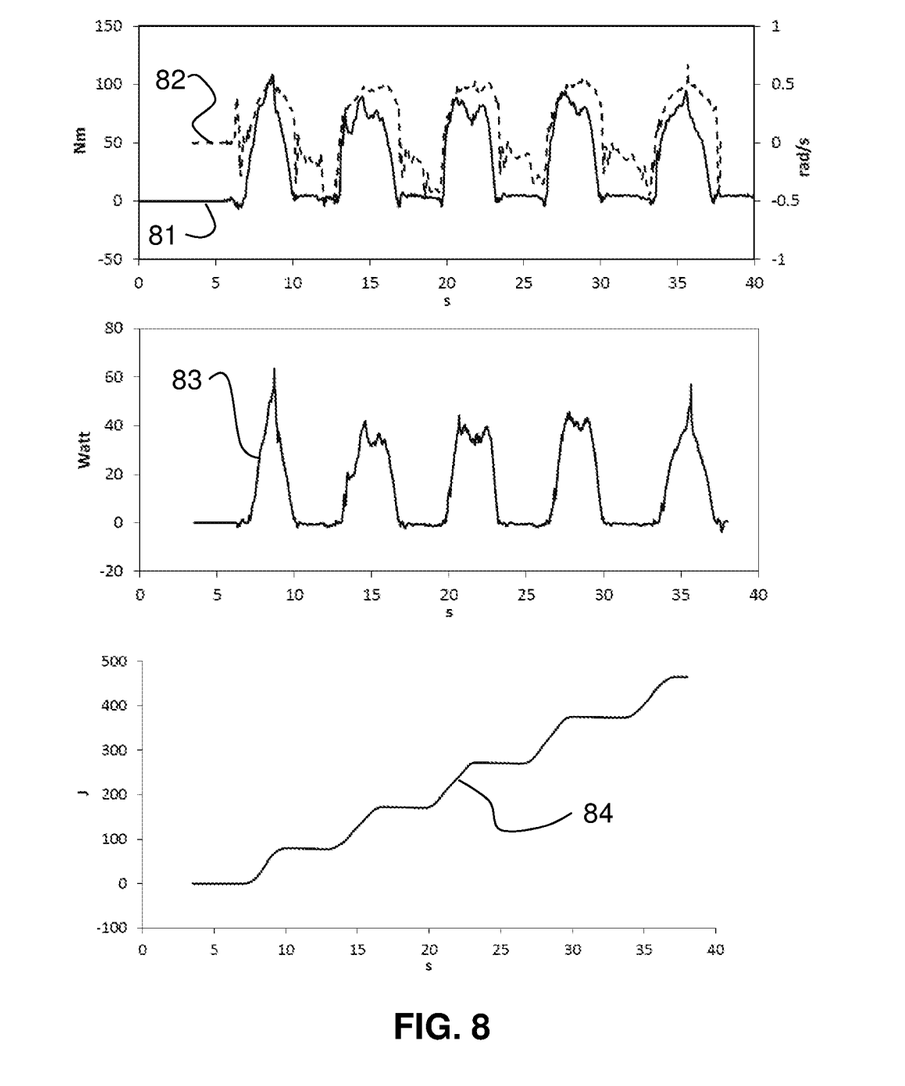
FIG. 8 shows a synopsis of a reduced version of FIG. 7 with values of power and work done over the five represented strokes resulting from an analysis.

FIG. 7 shows measurement graphs of torque 81 and rotation rate 82 of an oar during the practical operation of a measuring transducer according to FIG. 5, and FIG. 8 shows a synopsis of a reduced version of FIG. 7 with values of the power 83 and the work done 84 over the represented five strokes resulting from an analysis. FIG. 7 shows the measured torque over five strokes in Nm with peak values of approx. 100 Nm with the solid line 81. For the dashed graph 82, the measured rotation rate lies between +−0.5 rad/s according to the axis plotted on the right. The stroke rate was approx. 12.

FIG. 8 records the measured values of FIG. 7 again. Said values are shown in the top diagram of the three diagrams. Below this, the value of the current power 83 calculated from said values is shown to the same scale, having peak values between 40 and 60 Watts. Said value is of course not exactly zero when returning the oar, but the significant component is the five deflections resulting from pulling the oar blade through the water and thereby from a product of the two values of the torque 81 and the rotation rate 82. The bottom graph represents the summed work here, which changes during every stroke from a previous plateau value to a new plateau value, here approx. 100 Joules per rowing stroke.

| REFERENCE CHARACTER LIST | |
|---|---|
| 1 | oar shaft |
| 2 | oar blade |
| 3 | measuring sleeve |
| 4 | strain gauge (DMS) |
| 5 | DMS amplifier |
| 6 | microelectromechanical system (MEMS) |
| 7 | collar |
| 8 | ring |
| 9 | oar handle |
| 10 | part on the oar blade side |
| 11 | part on the oar handle side |
| 12 | recess on the oar blade side |
| 13 | recess on the oar handle side |
| 30 | central part |
| 31 | first connecting part |
| 32 | second connecting part |
| 33 | recess |
| 34 | recess |
| 35 | central bore |
| 36 | central axis |
| 37 | first supporting surface |
| 38 | second supporting surface |
| 39 | radial bore |
| 40 | cable |
| 50 | processing unit |
| 60 | energy source |
| 61 | receiver |
| 70 | central part |
| 71 | groove |
| 72 | groove |
| 73 | measuring transducer |
| 74 | recess |
| 77 | flat section |
| 78 | through hole |
| 79 | flat section |
| 81 | graph of the bending moment |
| 82 | graph of the rotation rate |
| 83 | graph of the power |
| 84 | graph of the work done |

The invention claimed is:

1. A system for determining a bending moment on an oar during a rowing stroke in the water comprising:
an oar handle;
an oar shaft that extends from the oar handle and that has at least two adjacent parts;
an oar blade that is disposed on the oar shaft on a side opposite the oar handle;
a measuring transducer;
at least one strain gauge;
a microelectromechanical system; and
at least one analysis circuit;
wherein the at least one analysis circuit is connected to the at least one strain gauge and to the microelectromechanical system and is designed to determine a bending moment of a bending moment vector over time from a measurement signal of the at least one strain gauge and to determine a rotation rate of the oar about an axis parallel to a bending moment vector against time from a measurement signal of the microelectromechanical system on the oar, wherein the oar shaft is of a multi-part form and the measuring transducer is disposed between two of the at least two adjacent parts of the oar shaft, connects the two of the at least two adjacent parts of the oar shaft to each other and comprises the at least one strain gauge, wherein the at least one analysis circuit is designed to determine a rowing power over time from a scalar product of the bending moment and the rotation rate.

2. The system according to claim 1, wherein the at least one strain gauge is disposed on a surface of the measuring transducer.

3. The system according to claim 1, wherein the measuring transducer has a cylindrical shape with a central axis and comprises a central part and two connecting parts for connecting to the two of the at least two adjacent parts of the oar shaft, wherein the two connecting parts are disposed on mutually opposite sides of the central part.

4. The system according to claim 3, wherein the two connecting parts are offset in relation to the central part and the central part forms a stop for the two of the at least two adjacent parts of the oar shaft, wherein the central part is fixed to the stop by a thread.

5. The system according to claim 3, wherein the measuring transducer comprises at least one recess for accommodating the at least one strain gauge on a periphery in the central part.

6. The system according to claim 5, wherein the measuring transducer comprises a radial slot that is oriented in a longitudinal direction of the measuring transducer, into which the at least one analysis circuit connected to the at least one strain gauge is inserted.

7. The system according to claim 6, wherein the measuring transducer comprises two mutually opposite recesses for accommodating one of the at least one strain gauge on an outer periphery in the central part in a direction of the central axis and the radial slot comprises at least one through opening to connect the at least one analysis circuit to one or more strain gauges that are disposed near the at least one through opening.

8. The system according to claim 7, wherein an energy source is inserted into the radial slot next to the at least one analysis circuit.

9. The system according to claim 5, wherein the measuring transducer comprises a central bore that extends along the central axis through the measuring transducer.

10. The system according to claim 9, wherein the at least one strain gauge is disposed on an inner surface of the central bore.

11. The system according to claim 1, wherein the oar shaft is in two parts and is divided into a part on a side of the oar blade and a part on a side of the oar handle, wherein the part on the side of the oar blade comprises a collar on an end thereof opposite the oar blade with a ring for attaching the oar to a rowing boat, and wherein the measuring transducer is subsequently joined to the collar with the part on the side of the oar blade.

12. The system according to claim 1, wherein the oar shaft is in two parts and is divided into a part on a side of the oar blade and a part on a side of the oar handle, wherein the part on the side of the oar handle on the end thereof opposite the oar handle comprises a collar with a ring for attaching the oar to a rowing boat and wherein the measuring transducer is subsequently joined to the collar with the part on the side of the oar handle.

13. The system according to claim 1, wherein the measuring transducer is glued into the two of the at least two adjacent parts of the oar shaft.

14. The system according to claim 1, further comprising
a processing unit that is electrically conductively connected by cable to the at least one strain gauge;
at least one energy source that is electrically conductively connected to the at least one strain gauge and the processing unit in order to supply said at least one strain gauge and processing unit with electrical energy;
wherein the processing unit comprises a strain gauge amplifier that is designed to amplify a signal that is produced by the at least one strain gauge and to transmit said signal wirelessly to at least one receiver.

15. The system according to claim 14, wherein the processing unit comprises the microelectromechanical system that is designed to measure a rotational motion of the oar and to transmit a corresponding signal wirelessly to at least one receiver.

16. The system according to claim 14, wherein the processing unit is disposed in the part of the oar shaft on the oar handle side.

17. The system according to claim 14, wherein the processing unit is disposed in the part of the oar shaft on the oar blade side.

18. The system according to claim 14, wherein the at least one receiver is a desktop, a laptop, a tablet, a smartwatch or a smartphone or wherein the at least one receiver is a memory unit, which can be connected to a desktop, a laptop, a tablet or a smartphone.

19. A method for determining the power on an oar during a rowing stroke in the water, comprising the following steps:
determining the bending moment on the oar against time by means of at least one strain gauge that is disposed on a measuring transducer that is disposed between two adjacent parts of an oar shaft of the oar and that connects said adjacent parts to each other;
determining a rotation rate against time of the oar about an axis parallel to a bending moment vector by a microelectromechanical system, which is disposed on the oar; and
determining the rowing power against time from the scalar product of the bending moment and the rotation rate.

* * * * *